United States Patent [19]
Graber

[11] Patent Number: 4,551,144
[45] Date of Patent: Nov. 5, 1985

[54] INCONTINENT CARE PAD METHOD AND APPARATUS

[76] Inventor: Helen E. Graber, Rte. 1, Box 14, Montrose, Minn. 55363

[21] Appl. No.: 497,952

[22] Filed: May 25, 1983

[51] Int. Cl.⁴ .............................................. A61F 13/16
[52] U.S. Cl. ................................................... 604/378
[58] Field of Search ............... 604/358, 378, 379, 380, 604/381, 382, 383, 385; 428/77, 79, 221; 128/155, 156

[56] References Cited

U.S. PATENT DOCUMENTS

| | | | |
|---|---|---|---|
| 1,533,973 | 4/1925 | Cohen et al. | 128/296 |
| 2,682,873 | 7/1954 | Evans et al. | 128/156 |
| 2,833,282 | 5/1958 | Moore | 604/378 |
| 3,709,221 | 1/1973 | Riely | 128/156 |
| 3,888,257 | 6/1975 | Cook et al. | 128/296 |
| 3,967,623 | 7/1976 | Butterworth et al. | 128/287 |
| 3,971,380 | 7/1976 | Tritsch | 604/378 |
| 4,077,410 | 3/1978 | Butterworth et al. | 128/287 |
| 4,097,973 | 7/1978 | O'Connell | 5/335 |
| 4,166,464 | 9/1979 | Korpman | 128/287 |
| 4,216,774 | 8/1980 | Graber | 128/296 |

*Primary Examiner*—John D. Yasko
*Assistant Examiner*—Christa K. Scott
*Attorney, Agent, or Firm*—Henderson & Sturm

[57] ABSTRACT

An incontinent care pad (10) having three layers and a method for making same. The top layer (11) provides a soft surface for patient contact. The second layer (12) provides a waterproof bottom. The third layer (13) comprises an absorbant inner material. The third layer connects to the first layer, but not to the second and the second layer connects to the first layer but not to the third.

4 Claims, 10 Drawing Figures

INCONTINENT CARE PAD METHOD AND APPARATUS

TECHNICAL FIELD

This invention relates generally to absorbant pads, and more particularly to reusable incontinent care pads.

BACKGROUND ART

Many persons suffer from temporary or chronic incontinency. Persons who are incontinent are incapable of controlling their excretory functions.

To care for such persons, absorbant pads are often placed beneath them while they sit or lie down. Most such pads are disposable. Once they have served their function, they may be thrown away.

Many problems are associated with such disposable pads. For instance, the absorbant material contained therein tends to bunch up. As a result, the pad may not be comfortable to the incontinent person. Such pads also have limited absorbency. Finally, such disposables tend to be relatively expensive for use over any extended period of time.

Non disposable pads tend to be somewhat more economical, since they may be reused following an appropriate washing and drying. Nevertheless, such pads often tend to suffer from some of the problems described above, such as bunching up. In addition, many such reusable pads tend to be relatively expensive to purchase. Manufacturing techniques employed to avoid the bunching up problem and to assure a long useful life can greatly increase the manufacturing costs, and hence the user cost, of the product.

There exists a need for a reusable incontinent care pad that will not tend to bunch up, that will be comfortable to the incontinent person, and that will provide appropriate absorbent characteristics. Preferably, such a pad should be relatively inexpensive to manufacture.

DISCLOSURE OF INVENTION

The instant invention substantially meets these needs. The pad of this invention comprises a first top layer, a second lower layer and a third inner layer. A first securement unit connects the first layer to the third, and a second securement unit connects the first layer to the second.

The first top layer should be soft, smooth, non-abrasive and substantially wrinkle-free, even after repeated washings. Such material should further act to transmit fluid therethrough and yet feel substantially dry on the outer surface thereof. Nylon or polyester both work well in this capacity.

The second bottom layer should be waterproof. This layer has a waterproof material affixed to one side thereof to form a waterproof barrier.

Finally, the third inner layer comprises an absorbant material such as a composite mixture of nylon and polyester fibers, or rayon fibers. Six ounce material works well in this capacity.

Both the first and second securement units may constitute threaded stitching. The first securement unit serves to bind the first top layer and the third inner absorbant layer to one another. The second securement unit serves to bind the top and bottom layers together.

BRIEF DESCRIPTION OF THE DRAWINGS

These and other attributes will become more clear upon a thorough review and study of the following description of the best mode for carrying out the invention, particularly when reviewed in conjunction with the drawings, wherein.

BEST MODE FOR CARRYING OUT THE INVENTION

Figure 1:
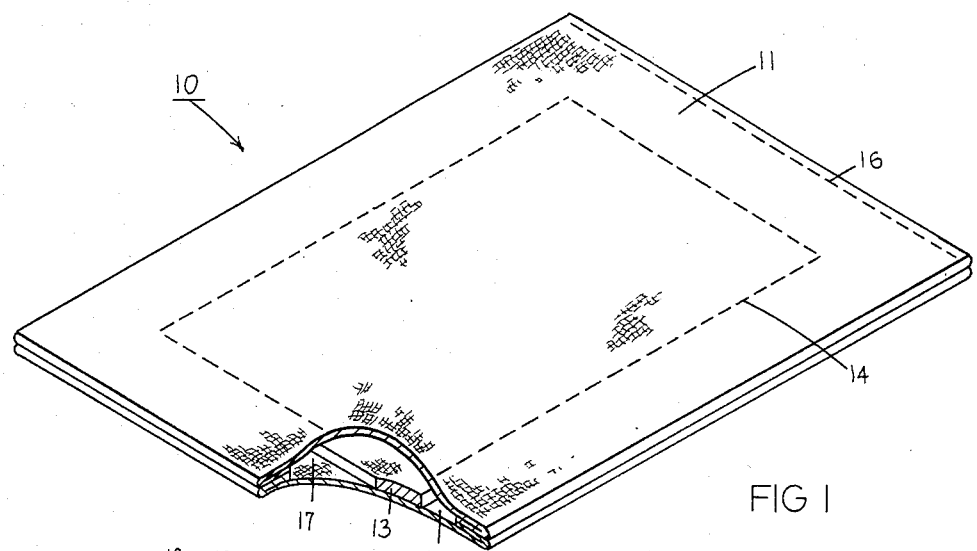
FIG. 1 comprises a perspective, enlarged, partially cut-away view of the pad.

Referring now to the drawings, and in particular to FIG. 1, the pad may be seen as depicted generally by the numeral 10. The pad (10) includes generally a first layer (11), a second layer (12) and a third layer (13). In addition, a first securement unit (14) serves to attach the first and third layers (11 and 13), and a second securement unit (16) serves to connect the first and second layers (11 and 12). Each of these layers and securement units will now be described in more detail in seriatim fashion.

The first layer (11) comprises a top layer. During use, this first layer (11) will be in direct contact with the incontinent patient. This layer (11) may be comprised of fibers made of polyesters or nylons. Nylon shall be understood to mean manufactured fibers characterized by any long chain synthetic polyamide having recurring amide groups as an integral part of the polymer chain. Polyester shall be understood to be a manufactured fiber characterized as any long chain synthetic polymer composed of at least 85% by weight of an ester of a dihydric alcohol and terephthalic acid.

The first layer (11) may be formed to any appropriate dimensions, such as twenty-four inches by twenty-four inches.

The second layer (12) comprises a waterproof bottom layer. This layer may also be comprised of nylon or polyester. A water impermeable substance may be coated on one side thereof (17) to prevent moisture from escaping through the underside of the pad (10).

The third layer (13) comprises an absorbant inner layer that may be ultimately disposed between the first and second layers (11 and 12). This inner layer may be comprised of a composite polyester and nylon mixture. In the alternative, rayon may also be utilized in an appropriate blend (it shall be understood that rayon refers to a manufactured fiber composed of regenerated cellulose in which substituents have replaced not more than 15% of the hydrogens of the hydroxyl groups). Multiple layers of such material may also be aligned co-planar with one another to form the inner absorbant layer (13).

The first and second securement unit (14 and 16) and the manufacture of the pad (10) will now be described.

Figure 2:
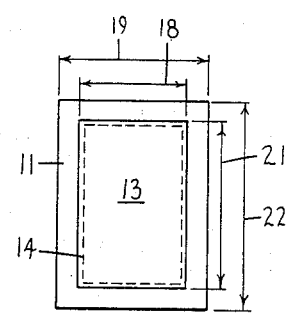
FIG. 2 comprises a bottom plan view of the third layer attached to the first layer.
Figure 3:
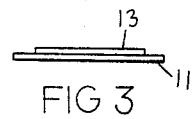
FIG. 3 provides a front elevational view of FIG. 2.
Figure 10:
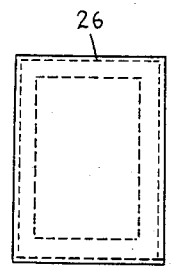
FIG. 10 provides a top plan view of the pad.

Referring to FIGS. 2 and 3, the first layer (11) has a greater width (19) than the width (18) of the third layer (13). In addition, the first layer (11) has a greater length (22) than the length (21) of the third layer (13). Consequently, with the inner layer (13) disposed substantially centrally upon the first layer (11), no edges of the inner layer (13) will meet or overlap any edges of the first layer (11).

So disposed, the first securement unit (14) may be utilized to connect the third inner layer (13) on all four edges to the first layer (11). The first securement unit (14) may be any suitable threaded stitching means.

Figure 4:
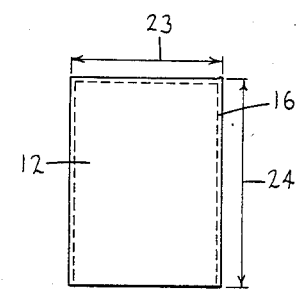
FIG. 4 comprises a top plan view of the pad with the second layer attached therethrough.
Figure 5:
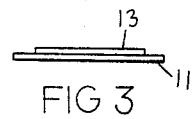
FIG. 5 comprises a front elevational view of FIG. 4.

Referring to FIGS. 4 and 5, the bottom layer (12) has a width (23) and a length (24) substantially equal to the width (19) and length (22) of the top layer (11).

The bottom layer (12) may be centrally disposed with respect to the top layer (11) on the side opposite the inner absorbant layer (13). Three sides of the top and bottom layers (11 and 12) may then be connected by the second securement unit (16). This connection may be by any appropriate threaded stitching.

Figure 6:
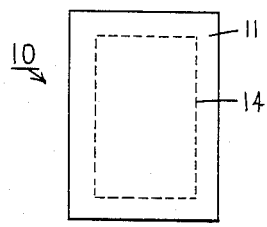
FIG. 6 provides a top plan view of the pad.
Figure 7:
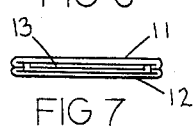
FIG. 7 provides a front elevational view of FIG. 6.

Referring to FIGS. 6 and 7, the pad (10) may then be turned inside out, such that the third layer (13) becomes disposed between the top and bottom layers (11 and 12).

Figure 8:
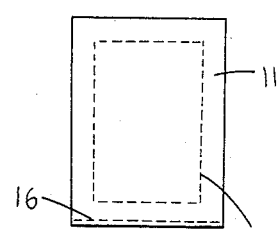
FIG. 8 provides a top plan view of the pad.
Figure 9:
FIG. 9 provides a front elevational view of FIG. 8.

Referring to FIGS. 8 and 9, the remaining unconnected edge between the first and second layers (11 and 12) may then be stitched together to complete the second securement unit (14).

If desired, this final stitching may be extended about the entire periphery of the pad (10) as indicated by the numeral 26.

By this configuration, it will be appreciated that the top layer (11) comprises a soft, comfortable surface for operable contact with the incontinent patient. The second layer (12) comprises a waterproof bottom to the pad (10). The absorbant inner layer (13) provides absorbency to absorb fluids as necessary.

The pad (10) may be washed and dried according to current institutional practices many times without diminishing its suitability for its intended purpose. Further, such washings do not tend to cause the absorbant inner layer to bunch up or to otherwise become less effective.

It should also be understood that the above benefits are obtained through a very simple manufacturing process. The simplicity of this manufacturing process contributes to a lower overall cost of manufacture, and hence, a lower priced product.

It should be understood that other means of connecting the various layers could be utilized, such as heat, ultrasound or adhesives, under appropriate circumstances.

Obviously, numerous modifications and variations of the present invention are possible in light of the above teachings. It is therefore to be understood that within the scope of the appended claims, the invention may be practiced otherwise than as specifically described therein.

I claim:
1. An incontinent care pad comprising:
   a top layer of soft liquid permeable non-abrasive material;
   a bottom layer of liquid repellant material secured about a substantial portion of the periphery thereof to said top layer;
   an inner layer of soft absorbent material having smaller lateral and longitudinal dimensions than said top layer, said inner layer being disposed directly between said top and bottom layers and attached to said top layer but not to said bottom layer whereby the inner layer can slide with respect to the bottom layer but not with respect to said top layer.

2. A method of making an incontinent care pad, the method including the following steps:
   (a) step 1—the securement of an absorbant layer of material along the periphery thereof to a soft, non-abrasive layer of material, said absorbant layer having smaller lateral and longitudinal dimensions than said soft, non-abrasive layer;
   (b) step 2—the securement of a water repellent layer of material to said soft, non-abrasive layer about part, but not all, of the periphery thereof on the side of said soft, non-abrasive layer opposite said absorbant layer;
   (c) step 3—everting said soft, non-absorbant layer and said water repellant layer to thereby place said absorbant layer between said soft, non-abrasive layer and said water repellent layer; and
   (d) step 4—the.securement of said soft, non-abrasive layer and said water repellent layer along the previously unconnected periphery thereof.

3. The apparatus of claim 1 wherein said inner layer connects to said top layer proximal the periphery of said inner layer.

4. The improvement of claim 3 wherein said top layer connects proximal the edges thereof to said bottom layer proximal the edges thereof.

* * * * *